(12) United States Patent
Tu et al.

(10) Patent No.: US 12,307,672 B2
(45) Date of Patent: May 20, 2025

(54) METHOD AND APPARATUS FOR CALCULATING BLOOD FLOW RATE IN CORONARY ARTERY, AND ELECTRONIC DEVICE

(71) Applicant: Shanghai Pulse Medical Technology, Inc., Shanghai (CN)

(72) Inventors: Shengxian Tu, Shanghai (CN); Qiuyang Zhao, Shanghai (CN); Juan Luis Gutiérrez-Chico, Shanghai (CN); Shuzhan Chen, Shanghai (CN)

(73) Assignee: Shanghai Pulse Medical Technology, Inc., Shanghai (CN)

( * ) Notice: Subject to any disclaimer, the term of this patent is extended or adjusted under 35 U.S.C. 154(b) by 328 days.

(21) Appl. No.: 17/802,838

(22) PCT Filed: Jan. 22, 2021

(86) PCT No.: PCT/CN2021/073277
§ 371 (c)(1),
(2) Date: Aug. 26, 2022

(87) PCT Pub. No.: WO2021/175039
PCT Pub. Date: Sep. 10, 2021

(65) Prior Publication Data
US 2023/0108647 A1   Apr. 6, 2023

(30) Foreign Application Priority Data
Mar. 2, 2020   (CN) .......................... 202010134217.7

(51) Int. Cl.
G06T 7/00 (2017.01)
G06T 7/11 (2017.01)
G06T 7/60 (2017.01)

(52) U.S. Cl.
CPC .............. *G06T 7/0016* (2013.01); *G06T 7/11* (2017.01); *G06T 7/60* (2013.01);
(Continued)

(58) Field of Classification Search
None
See application file for complete search history.

(56) References Cited

U.S. PATENT DOCUMENTS 10,282,841 B1 * 5/2019 Parsons-Wingerter ..................... G06T 7/0014
11,141,123 B2 * 10/2021 Homann ................ A61B 6/504
(Continued)

FOREIGN PATENT DOCUMENTS

CN   105096388 A   11/2015
CN   109065170 A   12/2018
(Continued)

OTHER PUBLICATIONS

Machine Translation of CN 110786840 A (Year: 2020).*
(Continued)

*Primary Examiner* — Michelle M Entezari Hausmann
(74) *Attorney, Agent, or Firm* — Barclay Damon LLP

(57) ABSTRACT

A method and apparatus for calculating the blood flow rate in a coronary artery, an electronic device and a storage medium. The method for calculating the blood flow rate in a coronary artery comprises the following steps: S1, acquiring an angiography image of the coronary artery, segmenting the angiography image of the coronary artery by using deep learning, and obtaining segmented images of a main vessel (S1); S2, calculating the length of the main vessel in each segmented image frame on the basis of the segmented
(Continued)

images of the main vessel (S2); and S3, obtaining the blood flow rate in the main vessel on the basis of the calculated change of the lengths of the main vessel with time (S3). By using the method and apparatus for calculating the blood flow rate in a coronary artery and the electronic device, the automation of the calculation of the blood flow rate in a coronary artery is achieved, the calculated blood flow rate in the coronary artery is more accurate, and the calculation method is simple.

18 Claims, 9 Drawing Sheets

(52) U.S. Cl.
CPC ............... *G06T 2207/20021* (2013.01); *G06T 2207/20084* (2013.01); *G06T 2207/20092* (2013.01); *G06T 2207/30048* (2013.01); *G06T 2207/30104* (2013.01)

(56) References Cited

U.S. PATENT DOCUMENTS

| | | | |
|---|---|---|---|
| 2008/0262346 A1* | 10/2008 | Assis | A61B 5/0275 600/431 |
| 2010/0172567 A1* | 7/2010 | Prokoski | A61B 5/418 348/47 |
| 2015/0269352 A1* | 9/2015 | Taylor | G16H 50/50 703/11 |
| 2017/0258433 A1 | 9/2017 | Gulsun et al. | |
| 2018/0235573 A1* | 8/2018 | Langeland | A61B 5/7425 |
| 2018/0310888 A1* | 11/2018 | Itu | G16H 50/50 |
| 2019/0155973 A1* | 5/2019 | Morczinek | G01C 11/04 |
| 2019/0261945 A1* | 8/2019 | Funka-Lea | G06T 15/205 |
| 2019/0387981 A1* | 12/2019 | Warner | A61B 5/0215 |
| 2021/0298706 A1* | 9/2021 | Tu | G06T 7/0014 |
| 2021/0382497 A1* | 12/2021 | Zhi | G06T 7/73 |

FOREIGN PATENT DOCUMENTS

| | | | | |
|---|---|---|---|---|
| CN | 109686450 A | | 4/2019 | |
| CN | 110335670 A | | 10/2019 | |
| CN | 110448319 A | | 11/2019 | |
| CN | 110674824 A | | 1/2020 | |
| CN | 110786840 A | * | 2/2020 | ............. A61B 34/10 |
| CN | 111369519 A | | 7/2020 | |

OTHER PUBLICATIONS

Ueda D, Shimazaki A, Miki Y. Technical and clinical overview of deep learning in radiology. Japanese journal of radiology. Jan. 25, 2019;37:15-33. (Year: 2019).*
Ronneberger, Olaf, Philipp Fischer, and Thomas Brox. "U-net: Convolutional networks for biomedical image segmentation."—MICCAI 2015: 18th international conference, proceedings, part III 18. Springer International Publishing, 2015. (Year: 2015).*
Chen, Xueying, Rong Zhang, and Pingkun Yan. "Feature fusion encoder decoder network for automatic liver lesion segmentation." 2019 IEEE 16th international symposium on biomedical imaging (ISBI 2019). IEEE, 2019. (Year: 2019).*
Sivasubramanian, Arrun, Jayanth Mohan, and V. Sowmya. "CASe_UNet: Multi-level Multi-scale UNet for Medical Image Segmentation." International Conference on Computer Vision, High-Performance Computing, Smart Devices, and Networks. Singapore: Springer Nature Singapore, 2023. (Year: 2023).*
Tsai TH, Huang SA. Refined U-net: A new semantic technique on hand segmentation. Neurocomputing. Jul. 21, 2022;495:1-0. (Year: 2022).*
Dinesh, P., and Ramanathan Lakshmanan. "Deep Learning-Driven Citrus Disease Detection: A Novel Approach with DeepOverlay L-UNet and VGG-RefineNet." (Year: 2024).*
Blaiech et al. "Impact of Enhancement for Coronary Artery Segmentation Based on Deep Learning Neural Network", Iberian Conference on Pattern Recognition and Image Analysis, pp. 261-263, Sep. 22, 2019.
International Searching Authority—International Search Report, pertaining to International Application No. PCT/CN2021/073277, dated Apr. 21, 2021, together with the Written Opinion of the International Searching Authority, 13 pages.
Lin et al, "RefineNet: Multi-Path Refinement Networks for High-Resolution Semantic Segmentation" The University of Adelaide, Australian Centre for Robotic Vision, arXiv:1611.06612 [cs.CV], Nov. 25, 2016 (11 pages).
CVPR 17 RefineNet: Multi-Path Refinement Networks for High-Resolution Semantic Segmentation, Sep. 30, 2018, English and Chinese, (6 pages).
Zhang, Yimin et al., "Automatic coronary blood flow computation: validation in quantitative flow ratio from coronary angiography", International Journal of Cardiovascular, Imaging, Kluwer Academic Publishers, Dordrecht, NL, vol. 35, No. 4,Dec. 8, 2018 (Dec. 8, 2018), pp. 587-595.
Office Action for Japanese Patent Application No. 2022-551789 dated Sep. 5, 2023, including English translation, (9 pages).
Extended European search report for European Patent Application No. 21765234.6, dated Aug. 11, 2023; (7 pages).

* cited by examiner

METHOD AND APPARATUS FOR CALCULATING BLOOD FLOW RATE IN CORONARY ARTERY, AND ELECTRONIC DEVICE

CROSS-REFERENCE TO RELATED APPLICATIONS

This application is a U.S. national phase entry under 35 USC § 371 of Patent Cooperation Treaty Application No. PCT/CN2021/073277 filed Jan. 22, 2021, which in turn claims priority from Chinese Patent Application 202010134217.7 filed Mar. 2, 2020. Each of the above-described applications is hereby incorporated herein by reference in their entire-ties.

TECHNICAL FIELD

The present invention relates to the technical field of computers, in particular to a method and apparatus for calculating the blood flow rate in a coronary artery, an electronic device and a computer storage medium.

BACKGROUND

In recent years, many methods for calculating FFR (fractional flow reserve) and CFR (coronary flow reserve) of a coronary artery on the basis of cardiovascular images have been proposed, wherein the blood flow rate in a coronary artery is an important condition for the calculation of FFR and CFR, and the current method for calculating the blood flow rate in a coronary artery mainly comprises the TIMI frame counting method, but the method requires manual measurement by a doctor and is complicated to operate.

SUMMARY

In order to solve the above technical problem, one object of the present invention is to provide a method for calculating the blood flow rate in a coronary artery, and by the calculation method, the automation of the calculation of the blood flow rate in a coronary artery is achieved, the calculated blood flow rate in a coronary artery is more accurate, and the calculation method is simple.

Another object of the present invention is to provide a method for calculating blood flow reserve in a coronary artery, comprising the method for calculating the blood flow rate in a coronary artery.

A third object of the present invention is to provide an apparatus for calculating the blood flow rate in a coronary artery used for implementing the method for calculating the blood flow rate in a coronary artery.

In order to achieve the above-mentioned objects, the present invention adopts the following technical solutions:

the method for calculating the blood flow rate in a coronary artery according to an embodiment of a first aspect of the present invention comprises:

S1, acquiring an angiography image of a coronary artery, segmenting the angiography image of the coronary artery by using deep learning, and obtaining segmented images of main vessel;

S2, calculating the length of the main vessel in each segmented image frame on the basis of the segmented images of the main vessel; and S3, obtaining the blood flow rate in the main vessel on the basis of the calculated change of the lengths of the main vessel with time.

Preferably, the S1 specifically comprises: acquiring the angiography image of the coronary artery, displaying type selection of the main vessel of the coronary artery, and segmenting the angiography image of the coronary artery by using deep learning on the basis of the type, selected by a user, of the main vessel to obtain the segmented images of the main vessel.

Preferably, the S1 further comprises: judging whether the projection angle of the angiography image of the coronary artery is within a required angle range of the main vessel of this type on the basis of the type, selected by the user, of the main vessel; wherein if the projection angle of the angiography image of the coronary artery is within the required angle range of the main vessel of this type, the angiography image of the coronary artery is segmented by using deep learning to obtain the segmented images of the main vessel; and if the projection angle of the angiography image of the coronary artery is not within the required angle range of the main vessel of this type, a prompt message is displayed.

Preferably, the step of segmenting the angiography image of the coronary artery by using deep learning to obtain the segmented images of the main vessel specifically comprises:

acquiring a plurality of feature maps with different resolutions of the angiography image of the coronary artery by means of an encoder structure of a U-Net model, and further refining and combining the plurality of feature maps with different resolutions by utilizing a RefineNet module to obtain the segmented images of the main vessel.

Preferably, the S2 specifically comprises:

S21, extracting the segmented images of the main vessel to obtain an angiography image of a blood vessel skeleton; and S22, calculating the length of the blood vessel skeleton in the angiography image of the blood vessel skeleton to obtain the lengths of the main vessel in pixels, and calculating in combination with a calibration factor of the image to obtain the actual physical length of the main vessel.

Preferably, the S3 specifically comprises:

S31, obtaining a change curve of the lengths of the main vessel with time by taking time as an abscissa and taking the lengths of the main vessel in the segmented images of the main vessel as an ordinate; and S32, selecting a preset section of the change curve of the lengths of the main vessel with time, and calculating the slope of the preset section to obtain the blood flow rate of the main vessel.

Preferably, the S31 specifically comprises:

S311, obtaining a change curve of the lengths of the main vessel with frame number by taking the frame number of the segmented images of the main vessel as an abscissa and taking the actual lengths of the main vessel as an ordinate; and S312, converting the abscissa in the change curve of the lengths of the main vessel with frame number into time on the basis of frame frequency information to obtain the change curve of the lengths of the main vessel with time.

Preferably, the S32 specifically comprises:

smoothing the change curve of the lengths of the main vessel with time to obtain a smooth curve of the change curve of the lengths of the main vessel with time;

obtaining the maximum value of the lengths of the main vessel on the smooth curve, and selecting the section, with the lengths of the main vessel on the smooth curve being a preset value of the maximum value of the lengths of the main vessel, as a preset section area, wherein the section, opposite to the preset section area on the smooth curve, of the change curve of the lengths of the main vessel with time is a preselected section;

judging whether the preselected section contains one cardiac cycle or not according to the electrocardio information of the coronary artery corresponding to the preselected section, wherein if the preselected section does not contain one cardiac cycle, it is determined that the preselected section is the preset section; and performing straight line fitting on the preset section, and calculating the slope of a straight line obtained by fitting to obtain the blood flow rate of the main vessel.

Preferably, if the preselected section contains one cardiac cycle, the preset section is obtained by extending toward two ends of the preselected section by the length of half of the cardiac cycle respectively by taking the center of the preselected section as a starting point.

Preferably, the change curve of the lengths of the main vessel with time, the angiography image of the coronary artery and the electrocardio information of the coronary artery corresponding to the angiography image of the coronary artery are displayed, and a user checks the angiography image of the coronary artery corresponding to the preset section, and the electrocardio information of the coronary artery, verifies the selected preset section, and manually adjusts the selected preset section if the preset section is unreasonably selected.

A method for calculating blood flow reserve in a coronary artery according to an embodiment of a second aspect of the present invention comprises:

calculating the blood flow rate of the main vessel in a resting state and the blood flow rate of the main vessel in a hyperemic state respectively by the method for calculating the blood flow rate in a coronary artery according to any one of the embodiments mentioned above, and obtaining the blood flow reserve of the coronary artery according to the calculated blood flow rate of the main vessel in the resting state and the calculated blood flow rate of the main vessel in the hyperemic state.

Preferably, by the method for calculating the blood flow rate in a coronary artery, the blood flow rate of the main vessel in the resting state and the blood flow rate of the main vessel in the hyperemic state are respectively calculated on the basis of the angiography image of the main vessel in the resting state and the angiography image of the coronary artery in the hyperemic state, wherein a time difference between the acquisition time of the angiography image of the coronary artery when the main vessel are in the resting state and the acquisition time of the angiography image of the coronary artery when the main vessel are in the hyperemic state is not greater than a first time threshold.

An apparatus for calculating the blood flow rate in a coronary artery according to an embodiment of a third aspect of the present invention comprises:

a coronary artery angiography image segmenting module, used for acquiring an angiography image of a coronary artery, segmenting the angiography image of the coronary artery by using deep learning, and obtaining segmented images of a main vessel;

a length calculating module, used for calculating the length of the main vessel in each segmented image frame on the basis of the segmented images of the main vessel; and a blood flow rate calculating module, used for obtaining the blood flow rate of the main vessel on the basis of the calculated change of the lengths of the main vessel with time.

Preferably, the apparatus for calculating the blood flow rate in a coronary artery further comprises a display apparatus, and the display apparatus is used for displaying type selection of the main vessel of the coronary artery for a user;

the coronary artery angiography image segmenting module is used for acquiring the angiography image of the coronary artery, and segmenting the angiography image of the coronary artery by using deep learning on the basis of the type, selected by the user, of the main vessel to obtain the segmented images of the main vessel.

Preferably, the coronary artery angiography image segmenting module is used for judging whether the projection angle of the angiography image of the coronary artery is within a required angle range of the main vessel of this type on the basis of the type, selected by the user, of the main vessel; wherein if the projection angle of the angiography image of the coronary artery is within the required angle range of the main vessel of this type, the angiography image of the coronary artery is segmented by using deep learning to obtain the segmented images of the main vessel; and if the projection angle of the angiography image of the coronary artery is not within the required angle range of the main vessel of this type, the display apparatus is used for displaying a prompt message for the user.

Preferably, the coronary artery angiography image segmenting module is used for acquiring feature maps with different resolutions of the angiography image of the coronary artery by means of an encoder structure of a U-Net model, and then refining and combining the feature maps with different resolutions by utilizing a RefineNet module to obtain the segmented images of the main vessel.

Preferably, the length calculating module is used for extracting the segmented images of the main vessel to obtain an angiography image of a blood vessel skeleton, calculating the length of the blood vessel skeleton in the angiography image of the blood vessel skeleton to obtain the lengths of the main vessel in pixels, and calculating in combination with a calibration factor of the image to obtain the actual physical length of the main vessel.

Preferably, the blood flow rate calculating module is used for obtaining a change curve of the lengths of the main vessel with time by taking time as an abscissa and taking the lengths of the main vessel in the segmented images of the main vessel as an ordinate, selecting a preset section of the change curve of the lengths of the main vessel with time, and calculating the slope of the preset section to obtain the blood flow rate of the main vessel.

Preferably, the blood flow rate calculating module is used for obtaining a change curve of the lengths of the main vessel with frame number by taking the frame number of the segmented images of the main vessel as an abscissa and taking the actual length of the main vessel as an ordinate, and converting the abscissa in the change curve of the lengths of the main vessel with frame number into time on the basis of frame frequency information to obtain the change curve of the lengths of the main vessel with time.

Preferably, the blood flow rate calculating module is used for smoothing the change curve of the lengths of the main vessel with time to obtain a smooth curve of the change curve of the lengths of the main vessel with time; obtaining the maximum value of the lengths of the main vessel on the smooth curve; selecting the section, with the lengths of the main vessel on the smooth curve being a preset value of the maximum value of the lengths of the main vessel, as a preset section area, wherein the section, opposite to the preset section area on the smooth curve, of the change curve of the lengths of the main vessel with time is a preselected section; judging whether the preselected section contains one cardiac cycle or not according to the electrocardio information of the coronary artery corresponding to the preselected section, wherein if the preselected section does not contain one cardiac cycle, it is determined that the preselected section is the preset section; and performing straight line fitting on the preset section, and calculating the slope of a straight line obtained by fitting to obtain the blood flow rate of the main vessel.

Preferably, if the preselected section contains one cardiac cycle, then the preset section is obtained by extending toward two ends of the preselected section by the length of half of the cardiac cycle respectively by taking the center of the preselected section as a starting point.

Preferably, the apparatus for calculating the blood flow rate in a coronary artery further comprises a display apparatus, the display apparatus is used for displaying the change curve of the lengths of the main vessel with time, the angiography image of the coronary artery and the electrocardio information of the coronary artery corresponding to the angiography image of the coronary artery for the user, and the user checks the angiography image of the coronary artery corresponding to the preset section, and the electrocardio information of the coronary artery, verifies the selected preset section, and manually adjusts the selected preset section if the preset section is unreasonably selected.

An electronic device for calculating the blood flow rate in a coronary artery according to an embodiment of the fourth aspect of the present invention comprises: one or more processors; and one or more memories, storing computer readable codes, wherein the computer readable codes implement the method for calculating the blood flow rate in a coronary artery according to any one of the embodiments mentioned above when executed by the one or more processors.

A computer storage medium according to an embodiment of a fifth aspect of the present invention stores computer readable codes, and the computer readable codes implement the method for calculating the blood flow rate in a coronary artery according to any one of the embodiments mentioned above when executed by one or more processors.

The beneficial effects of the prevent invention lie in that: the angiography image of the coronary artery is segmented by using deep learning to obtain the segmented images of the main vessel, the length of the main vessel in each image frame are calculated, then the blood flow rate of the main vessel is obtained on the basis of the change of the lengths of the main vessel with time, by the calculation method, the automation of the calculation of the blood flow rate of the coronary artery is realized, the calculated blood flow rate of the coronary artery is more accurate, and the calculation method is simple.

The foregoing description is only an overview of the technical solutions of the present invention, and in order to enable the technical means of the present invention to be more clearly understood and be implemented in accordance with the contents of the description, preferred embodiments of the present invention will be described in detail below in conjunction with the accompanying drawings.

DETAILED DESCRIPTION

The specific embodiments of the present invention will be described in further detail below in conjunction with the accompanying drawings and embodiments. The following embodiments are only intended to illustrate the present invention, but are not intended to limit the scope of the present invention.

It will be appreciated that as used herein, the term "module" can refer to or include an application specific integrated circuit (ASIC), an electronic circuit, a processor (shared, dedicated, or group) and/or memory that executes one or more software or firmware programs, a combinational logic circuit, and/or other suitable hardware components that provide the described functionality, or can be part of these hardware components.

It will be appreciated that in embodiments of the present invention, the processor can be a microprocessor, a digital signal processor, a microcontroller, or the like, and/or any combination thereof. According to another aspect, the processor can be a single-core processor, a multi-core processor, and the like, and/or any combination thereof.

Figure 1:
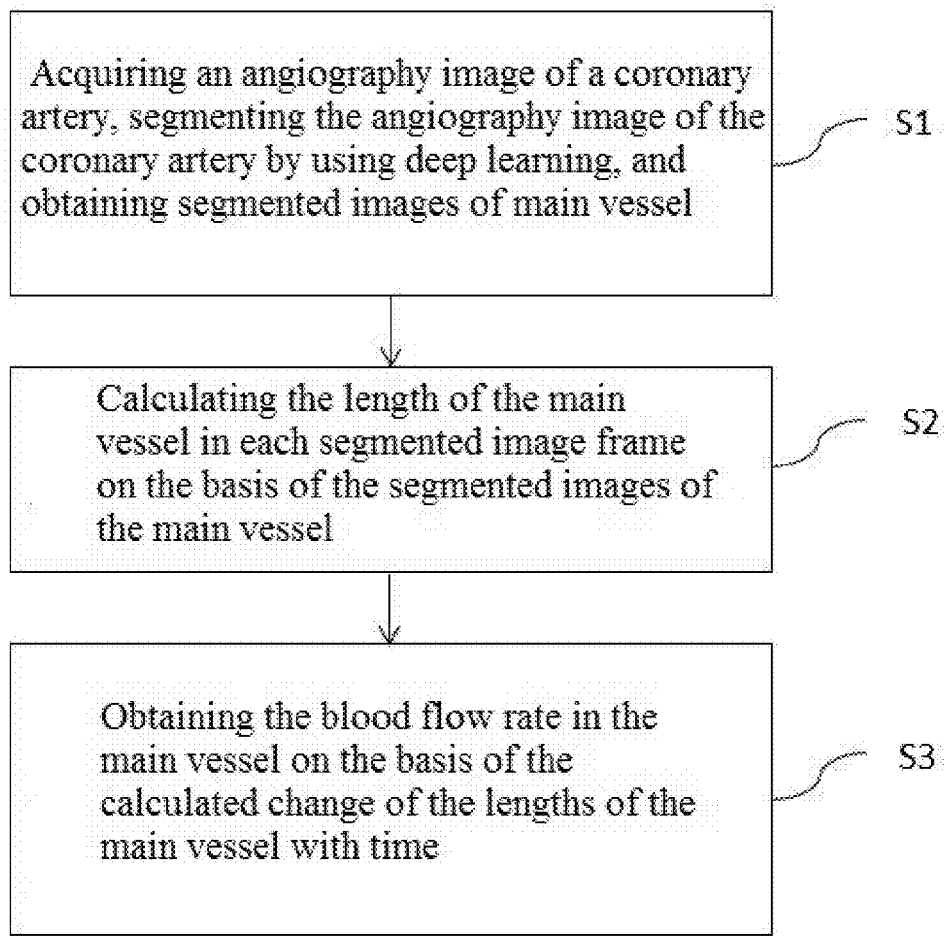
FIG. 1 is a flowchart of a method for calculating the blood flow rate in a coronary artery according to an embodiment of the present invention.

As shown in FIG. 1, a method for calculating the blood flow rate in a coronary artery according to an embodiment of the present invention comprises the following steps.

S1, acquiring an angiography image of the coronary artery, segmenting the angiography image of the coronary artery by using deep learning, and obtaining segmented images of main vessel.

Specifically, since only the blood flow rate in main vessel is paid attention to when the blood flow rate of a coronary artery is calculated, only the main vessel in the angiography image of the coronary artery need to be segmented to obtain segmented images of the main vessel. However, the traditional image processing methods such as Gabor filtering and Hessian matrix are very sensitive to all blood-vessel-like structures and cannot distinguish main vessel from side vessels. Therefore, a method of deep learning is utilized, the main vessel and the side vessels are distinguished by utilizing the strong characteristic extraction capability of the deep neural network, and only the main vessel is segmented, so that the subsequent process of calculating the lengths of the main vessel is greatly simplified.

Figure 2:
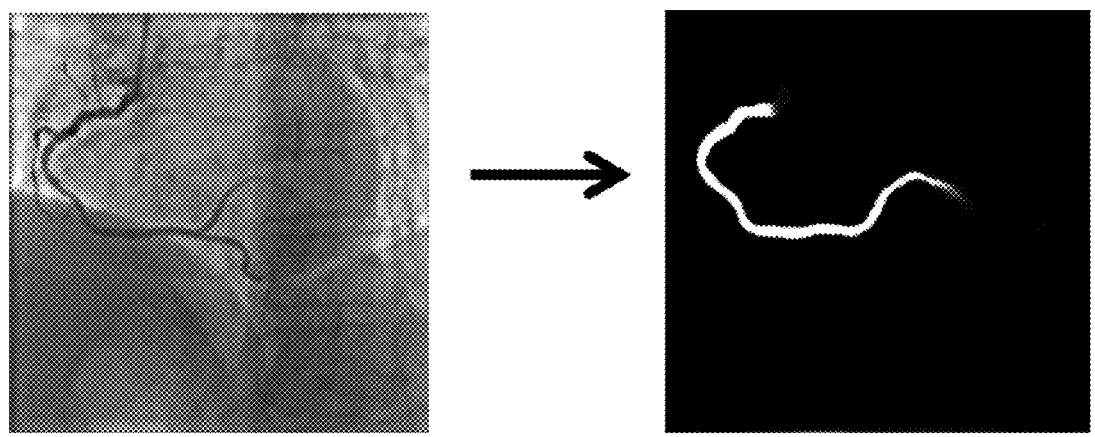
FIG. 2 is a schematic diagram of segmenting an angiography image of a coronary artery to obtain segmented images of main vessel.

As shown in FIG. 2, each frame of the acquired angiography image of the coronary artery is used as an input of a deep neural network, the deep neural network outputs a segmented image, having the same size as the original image, of a main vessel, the segmented image of the main vessel has a pixel value of 1 (shown in white in FIG. 2) at a position corresponding to the position of the main vessel on the original image, and has a pixel value of 0 (shown in black in FIG. 2) at other positions.

Preferably, the S1 specifically comprises: acquiring the angiography image of the coronary artery, displaying type selection of the main vessel of the coronary artery, and segmenting the angiography image of the coronary artery by using deep learning on the basis of the type, selected by a user, of the main vessel to obtain the segmented images of the main vessel.

Specifically, the main vessel of the coronary artery comprise an anterior descending branch blood vessel, a circumflex branch blood vessel and a right coronary artery blood vessel, a display apparatus can be used for displaying for the user which specific main vessel is selected from the anterior descending branch blood vessel, the circumflex branch blood vessel and the right coronary artery blood vessel, and the angiography image of the coronary artery is segmented by using deep learning according to the type, selected by the user, of the main vessel to obtain the segmented images of a certain main vessel. In addition, in other embodiments of the present invention, the type of the main vessel can be automatically identified from the angiography image of the coronary artery, and then the angiography image of the coronary artery can be segmented by using deep learning to obtain the segmented images of a certain main vessel.

Preferably, the S1 further comprises: judging whether the projection angle of the angiography image of the coronary artery is within a required angle range of the main vessel of this type or not on the basis of the type, selected by the user, of the main vessel; wherein if the projection angle of the angiography image of the coronary artery is within the required angle range of the main vessel of this type, the angiography image of the coronary artery is segmented by using deep learning to obtain segmented images of the main vessel; and if the projection angle of the angiography image of the coronary artery is not within the required angle range of the main vessel of this type, a prompt message is displayed.

Figure 9:
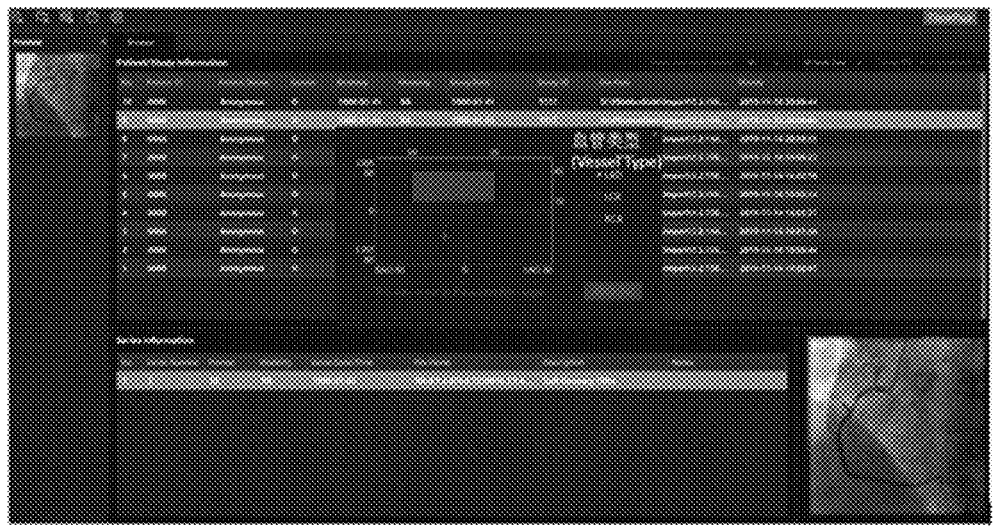
FIG. 9 is a schematic diagram of a first display interface displayed by a display apparatus according to an embodiment of the present invention.

Specifically, as shown in FIG. 9, after the angiography image of the coronary artery is acquired, a display apparatus can be used for displaying the type selection of the main vessel of the coronary artery for the user, whether the projection angle of the angiography image of the coronary artery is within the required angle range of the main vessel of this type or not is judged on the basis of the type, selected by the user, of the main vessel, wherein if the projection angle of the angiography image of the coronary artery is not within the required angle range of the main vessel of this type, the display apparatus displays the prompt message for the user to prompt that the projection angle of the angiography image of the coronary artery is not within the acceptable angle range of the main vessel of this type.

The accuracy of the calculated blood flow rate of the main vessel can be ensured by judging whether the projection angle of the angiography image of the coronary artery is within the required angle range of the main vessel of this type or not.

Preferably, the step of segmenting the angiography image of the coronary artery by using deep learning to obtain the segmented images of the main vessel specifically comprises:

acquiring a plurality of feature maps with different resolutions of the angiography image of the coronary artery by means of an encoder structure of a U-Net model, and further refining and combining the plurality of feature maps with different resolutions by utilizing a RefineNet module to obtain the segmented images of the main vessel.

Figure 3:
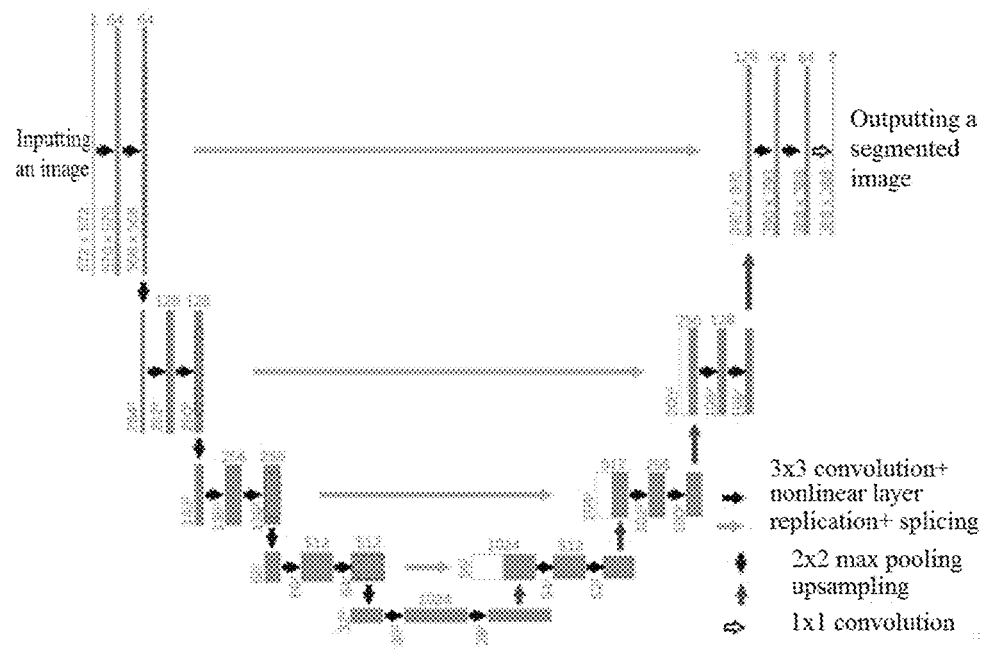
FIG. 3 is a structural schematic diagram of an existing U-Net model.

Specifically, an existing U-Net model utilizes the structure of an encoder-decoder, as shown in FIG. 3, an original image is convolved twice to obtain a 64-channel feature map, the resolution of the feature map is the same as that of the original image, the resolution of the 64-channel feature map is reduced to half of the original resolution by a max pooling operation, features are further extracted by convolution to obtain a 128-channel feature map of a second layer, and the above processes are repeated to obtain five feature maps with different resolutions, which is an encoding process, the process aims to extract high-level semantic information (low-resolution feature map) and low-level structural information (high-resolution feature map), then a decoding process is entered, the low-resolution feature map is upsampled to a high-resolution feature map, and the high-resolution feature map is spliced with the high-resolution feature map of the previous stage, after features are extracted by convolution, and upsampling and splicing operations are carried out again until the feature map is spliced with the feature map with the highest resolution, and the number of channels is adjusted by 1×1 convolution to obtain the required segmentation result.

Figure 4:
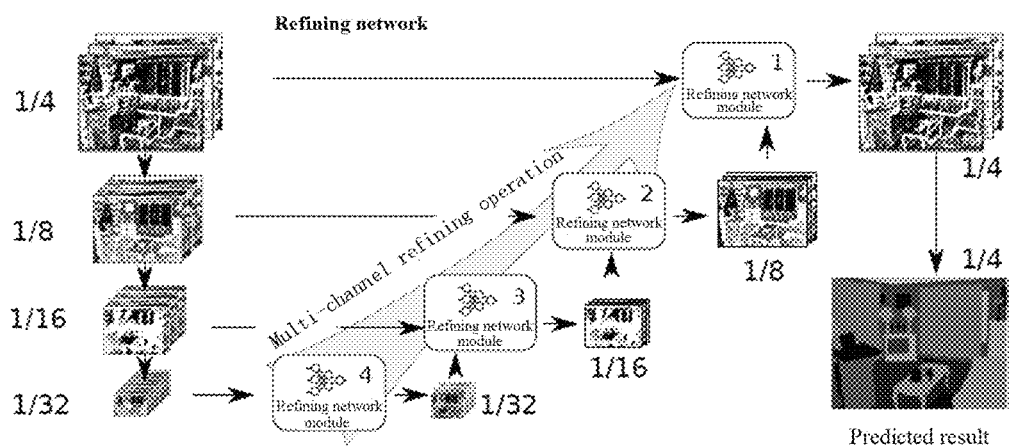
FIG. 4 is a structural schematic diagram of an existing RefineNet model.

An existing RefineNet model is similar to the U-Net model, and as shown in FIG. 4, the existing RefineNet model can receive feature map inputs of different scales, and combine and refine the feature maps of different scales, so that the feature maps can be conveniently processed subsequently.

The existing RefineNet model is mainly different from the U-Net model in two aspects: an encoder of the RefineNet model uses a ResNet structure popular in the semantic segmentation field, and an encoder of the U-Net model simply uses convolution to extract features; and the RefineNet model uses an original RefineNet module in the decoder, and the module can better refine information of the low-resolution feature map and the high-resolution feature map.

Figure 5:
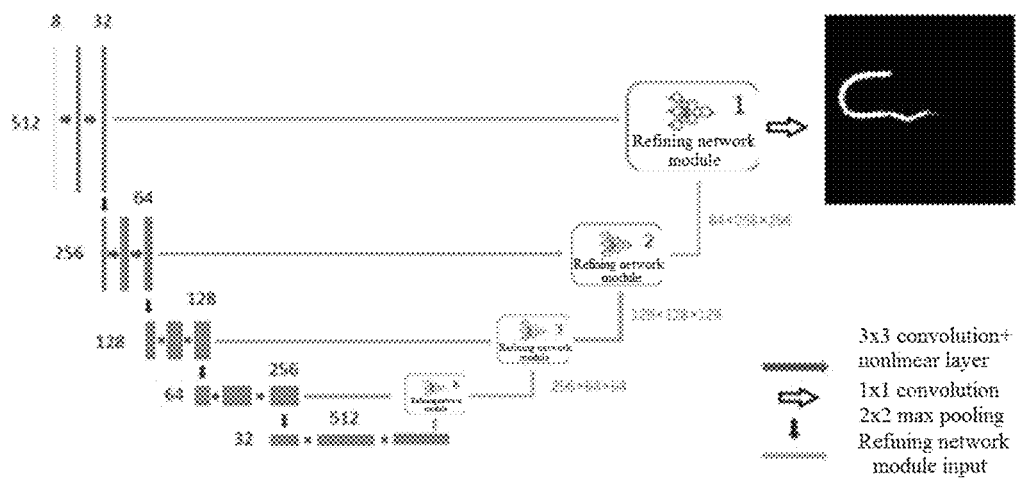
FIG. 5 is a structural schematic diagram of Refine-UNet used for segmenting an angiography image of a coronary artery according to an embodiment of the present invention.

FIG. 5 shows a structural schematic diagram of Refine-UNet used for segmenting the angiography image of the coronary artery in the present invention, and it should be noted that the types of feature maps with different resolutions of the angiography image of the coronary artery obtained by the encoder structure of the U-Net model are determined according to actual needs, for example, 5 types, 3 types, 7 types, and the like can be used.

The encoder structure of the U-Net model only uses convolution to obtain feature maps with different resolutions of the angiography image of the coronary artery, thereby avoiding waste of calculating resources and increasing the calculating speed; and the RefineNet module is utilized to refine and then combine the feature maps with high resolution and low resolution, thereby more efficiently utilizing high-level semantic information and low-level structural information and enhancing the accuracy of segmentation.

S2, calculating the length of the main vessel in each segmented image frame on the basis of the segmented images of the main vessel.

Preferably, the S2 specifically comprises:

S21, extracting the segmented images of the main vessel to obtain an angiography image of a blood vessel skeleton.

Figure 6:
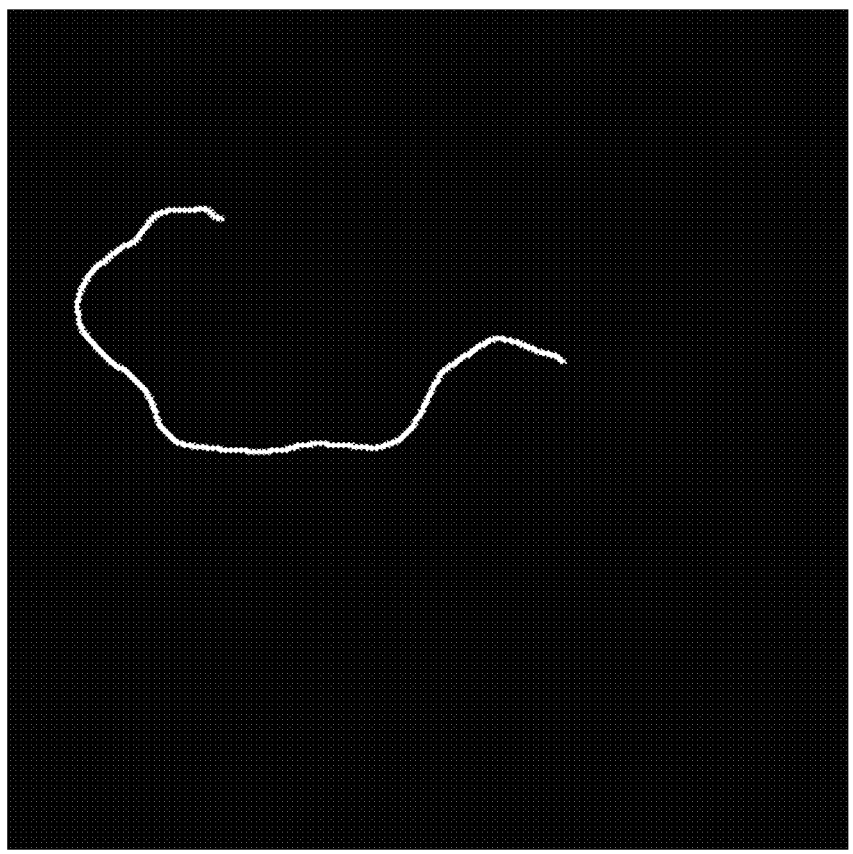
FIG. 6 shows an angiography image of a single-pixel-width blood vessel skeleton obtained by extracting segmented images of main vessel according to an embodiment of the present invention.

Specifically, as shown in FIG. 6, the obtained segmented images of the main vessel can be extracted to obtain the single-pixel-width angiography image of the blood vessel skeleton.

S22, calculating the length of the blood vessel skeleton in the angiography image of the blood vessel skeleton to obtain the lengths of the main vessel in pixels, and calculating in combination with the calibration factor of the image to obtain the actual physical length of the main vessel.

Specifically, the length of the blood vessel skeleton in the angiography image of the blood vessel skeleton can be calculated by a Fast Marching algorithm.

The angiography image of the blood vessel skeleton is obtained by extraction, the length of the blood vessel skeleton in the angiography image of the blood vessel skeleton is calculated to obtain the length of the main vessel, the accuracy of the calculated length of the main vessel is improved, and the accuracy of the calculated blood flow rate of the coronary artery is also improved.

S3, obtaining the blood flow rate of the main vessel on the basis of the calculated change of the lengths of the main vessel with time.

Figure 7:
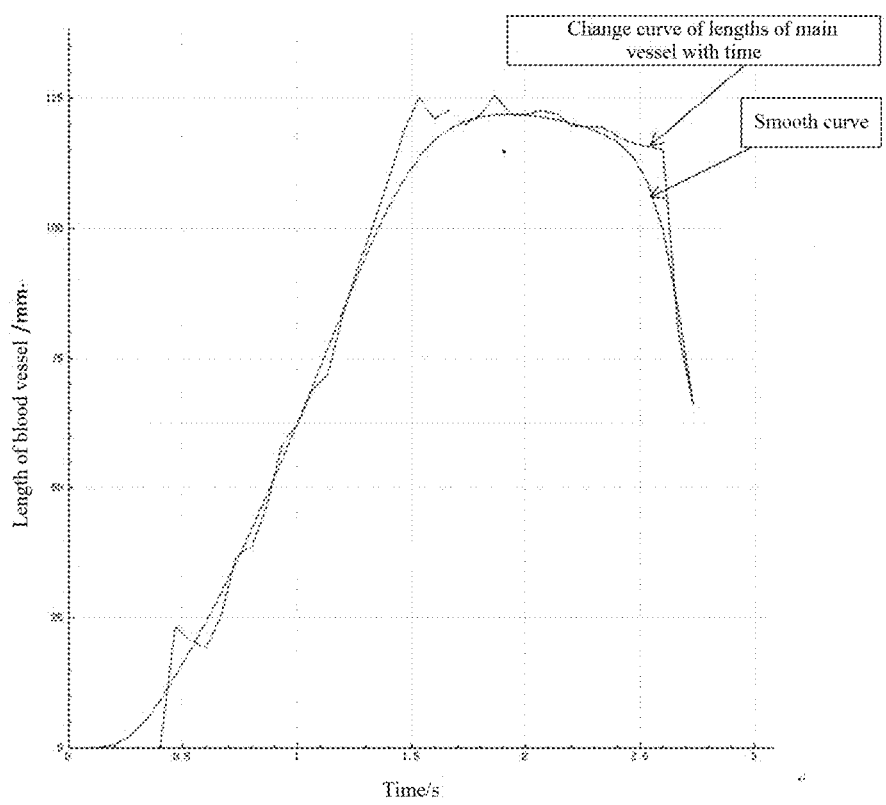
FIG. 7 is a schematic diagram of a change curve over time to lengths of main vessel and a smooth curve according to an embodiment of the present invention.

Preferably, the S3 specifically comprises:

S31, obtaining a change curve of the lengths of the main vessel with time by taking time as an abscissa and taking the lengths of the main vessel in the segmented images of the main vessel as an ordinate;

specifically, as shown in FIG. 7, the change curve of the lengths of the main vessel with time generally presents a gentle-ascending-gentle "S" shape, in the front section of the sequence of the angiography image of the coronary artery, the main vessel are invisible under X-ray due to the fact that a contrast agent is not injected into the coronary artery, the calculated lengths of the main vessel are generally 0 at the moment, and in the rear section of the sequence of the angiography image of the coronary artery, filling of the contrast agent in the coronary artery is finished, and the calculated lengths of the main vessel are the complete lengths of the main vessel and do not change.

Preferably, the S31 specifically comprises:

S311, obtaining a change curve of the lengths of the main vessel with frame number by taking the frame number of the segmented images of the main vessel as an abscissa and taking the actual lengths of the main vessel as an ordinate; and S312, converting the abscissa in the change curve of the lengths of the main vessel with frame number into time on the basis of frame frequency information to obtain the change curve of the lengths of the main vessel with time.

S32, selecting a preset section of the change curve of the lengths of the main vessel with time, and calculating the slope of the preset section to obtain the blood flow rate of the main vessel.

Preferably, the S32 specifically comprises:

S321, smoothing the change curve of the lengths of the main vessel with time to obtain a smooth curve of the change curve of the lengths of the main vessel with time.

Specifically, due to heart beat, blood vessel segmentation error and other reasons, a certain noise generally exists on the change curve of the lengths of the main vessel with time, so that the change curve of the lengths of the main vessel with time can be smoothed, and a K-order bezier curve can be used for smoothing the change curve of the lengths of the main vessel with time.

S322, obtaining the maximum value of the lengths of the main vessel on the smooth curve, and selecting the section, with the lengths of the main vessel on the smooth curve being a preset value of the maximum value of the lengths of the main vessel, as a preset section area, wherein the section, opposite to the preset section area on the smooth curve, of the change curve of the lengths of the main vessel with time is a preselected section.

Preferably, the minimum value of the preset value can be 0-20%, and the maximum value of the preset value can be 80-90%.

S323, judging whether the preselected section contains one cardiac cycle or not according to electrocardio information of the coronary artery corresponding to the preselected section, wherein if the preselected section does not contain one cardiac cycle, it is determined that the preselected section is the preset section.

Figure 8:
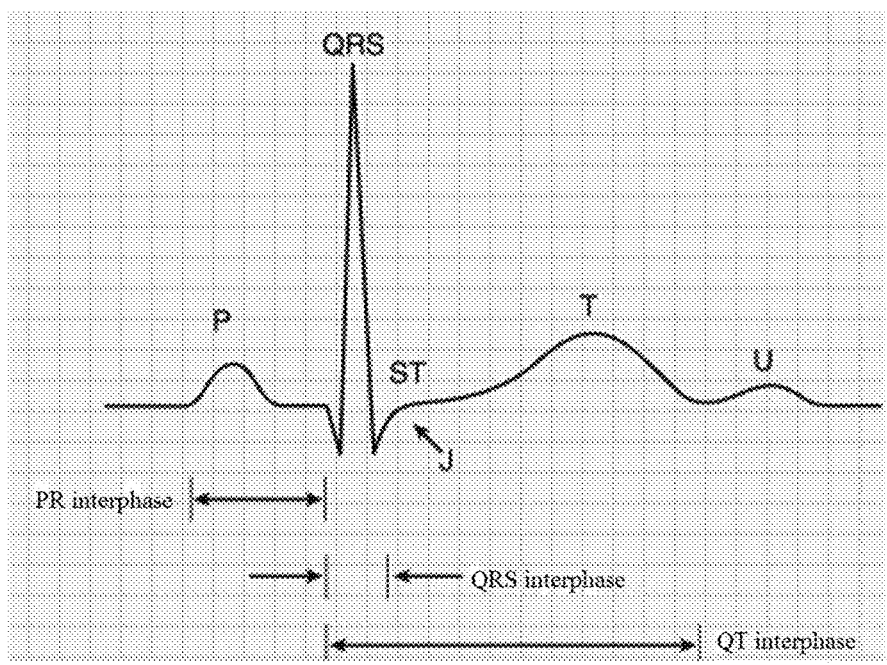
FIG. 8 shows an electrocardiogram in one cardiac cycle.

Specifically, the electrocardiogram of a normal cardiac cycle is shown in FIG. 8, wherein fluctuation of QRS wave is significantly higher than that of other waves, the peak of the QRS wave can be detected quickly by using a threshold or other methods, and the time of one cardiac cycle can be obtained according to the time interval between two adjacent QRS waves.

S324, performing straight line fitting on the preset section, and calculating the slope of a straight line obtained by fitting to obtain the blood flow rate of the main vessel.

Specifically, a linear least square method is used for performing straight line fitting on the preset section, and the slope of the straight line obtained by fitting is the blood flow rate of the main vessel.

Therefore, the preset section of the change curve of the lengths of the main vessel with time is obtained by the above method, and the blood flow rate of the main vessel is further obtained, so that the calculated blood flow rate of the main vessel is more accurate.

Preferably, if the preselected section contains one cardiac cycle, then the preset section can be obtained by extending toward two ends of the preselected section by the length of half of the cardiac cycle respectively by taking the center of the preselected section as a starting point.

Specifically, since the blood flow rate of the main vessel generally has differences at different stages of the cardiac cycle, a section of the change curve of the lengths of the main vessel with time corresponding to one cardiac cycle is used as the preset section, so that the calculated blood flow rate of the main vessel is more accurate.

The angiography image of the coronary artery is segmented by using deep learning to obtain the segmented images of the main vessel, the length of the main vessel in each image frame are calculated, then the blood flow rate of the main vessel is obtained on the basis of change of the lengths of the main vessel with time, by the calculation method, the automation of the calculation of the blood flow rate of the coronary artery is realized, the calculated blood flow rate of the coronary artery is more accurate, and the calculation method is simple.

Preferably, the change curve of the lengths of the main vessel with time, the angiography image of the coronary artery and the electrocardio information of the coronary artery corresponding to the angiography image of the coronary artery are displayed, and a user checks the angiography image of the coronary artery corresponding to the preset section, and the electrocardio information of the coronary artery, verifies the selected preset section, and manually adjusts the selected preset section if the preset section is unreasonably selected.

Figure 10:
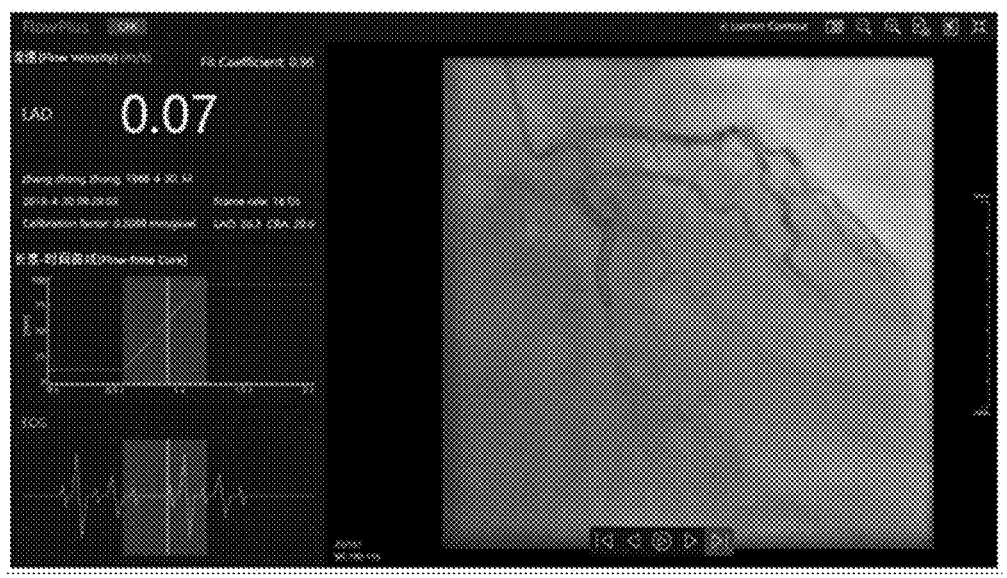
FIG. 10 is a schematic diagram of a second display interface displayed by a display apparatus according to an embodiment of the present invention.
Figure 11:
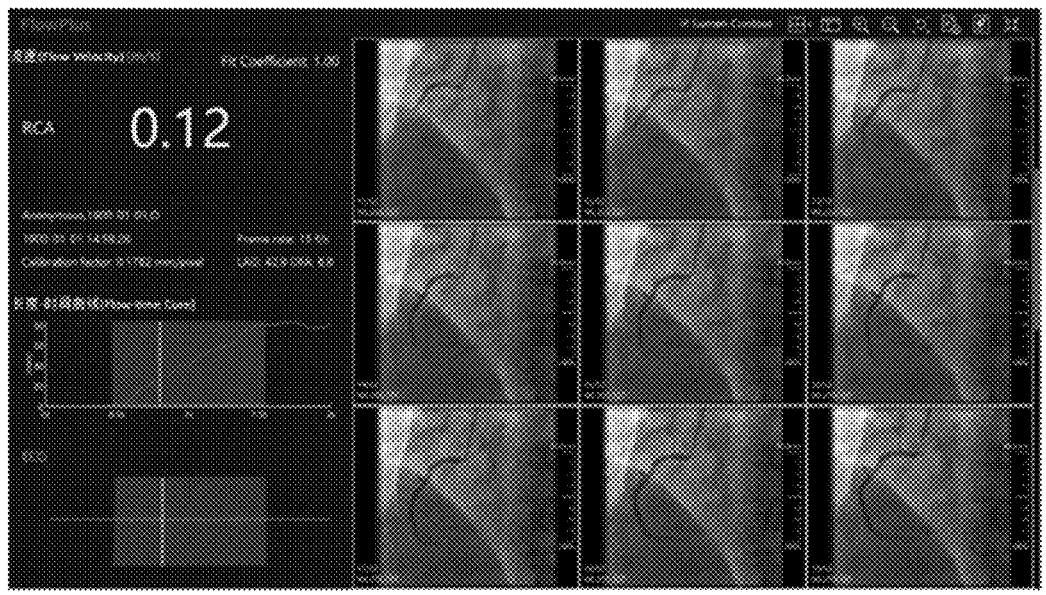
FIG. 11 is a schematic diagram of a third display interface displayed by a display apparatus according to an embodiment of the present invention.

Specifically, as shown in FIG. 10 and FIG. 11, a display apparatus can be used for displaying the change curve of the lengths of the main vessel with time and the electrocardio information of the coronary artery corresponding to the change curve for the user, the blood flow rate, obtained by performing straight line fitting on the preset section, of the main vessel is displayed, as shown in FIG. 10, the user can check different frames of the angiography image of the coronary artery by scrolling a mouse wheel or clicking any position on the change curve in a right image window of a display interface, as shown in FIG. 11, the right image window of the display interface can also be switched to a multi-window mode by clicking a certain function icon by means of a mouse, so as to check the angiography image of the coronary artery corresponding to the preset section, the selected preset section is verified, if the selected preset section is unreasonable, the selected preset section is adjusted manually, and the blood flow rate, displayed on the display interface, of the main vessel is updated in real time according to the selected preset section.

When the user thinks that an automatically selected preset section is unreasonably selected, the user can manually adjust the selected preset section, so as to ensure the reasonability of the selected preset section and further ensure that the blood flow rate of the coronary artery is more accurate.

A method for calculating blood flow reserve of a coronary artery comprising the method for calculating the blood flow rate of a coronary artery comprises the following steps:

calculating the blood flow rate of the main vessel in a resting state and the blood flow rate of the main vessel in a hyperemic state by the method for calculating the blood flow rate in a coronary artery according to any one of the embodiments mentioned above, and obtaining the blood flow reserve of the coronary artery according to the calculated blood flow rate of the main vessel in the resting state and the calculated blood flow rate of the main vessel in the hyperemic state.

Figure 12:
FIG. 12 is a schematic diagram of a fourth display interface displayed by a display apparatus according to an embodiment of the present invention.
Figure 13:
FIG. 13 is a schematic diagram of a fifth display interface displayed by a display apparatus according to an embodiment of the present invention.

Specifically, one sequence of the angiography image of the coronary artery is selected, the blood flow rate of the main vessel in one state is calculated by using the method for calculating the blood flow rate in a coronary artery, as shown in FIG. 12, an icon (CFR icon) for calculating blood flow reserve of the coronary artery on the display interface of the display apparatus is clicked, then, another sequence of the angiography image of the coronary artery is selected, the state of the main vessel in the other sequence of the angiography image of the coronary artery is opposite to the state of the main vessel in the one sequence of the angiography image of the coronary artery, the display apparatus displays the type selection of the state (a resting state or a hyperemic state) of the main vessel in the other sequence of the angiography image of the coronary artery for the user, the state of the main vessel in the one sequence of the angiography image of the coronary artery is determined according to the selection of the user, then the blood flow rate of the main vessel in another state is calculated, the blood flow reserve of the coronary artery is obtained according to the calculated blood flow rate of the main vessel in the resting state and the calculated blood flow rate of the main vessel in the hyperemic state, and as shown in FIG. 13, the blood flow reserve of the coronary artery is displayed.

Preferably, by the method for calculating the blood flow rate in a coronary artery, the blood flow rate of the main vessel in the resting state and the blood flow rate of the main vessel in the hyperemic state are respectively calculated on the basis of the angiography image of the main vessel in the resting state and the angiography image of the coronary artery in the hyperemic state, wherein a time difference between the acquisition time of the angiography image of the coronary artery when the main vessel are in the resting state and the acquisition time of the angiography image of the coronary artery when the main vessel are in the hyperemic state is not greater than a first time threshold.

Specifically, the first time threshold can be 7 days, or 15 days, or the like and is determined according to the actual situation, and the time difference between the acquisition time of the angiography image of the coronary artery when the main vessel are in the resting state and the acquisition time of the angiography image of the coronary artery when the main vessel are in the hyperemic state is not greater than the first time threshold, so that the accuracy of the calculated blood flow reserve of the coronary artery can be ensured.

By the method for calculating the blood flow reserve of the coronary artery, the automation of the calculation of the blood flow reserve of the coronary artery is realized, the calculated blood flow reserve of the coronary artery is more accurate, and the calculation method is simple.

Figure 14:
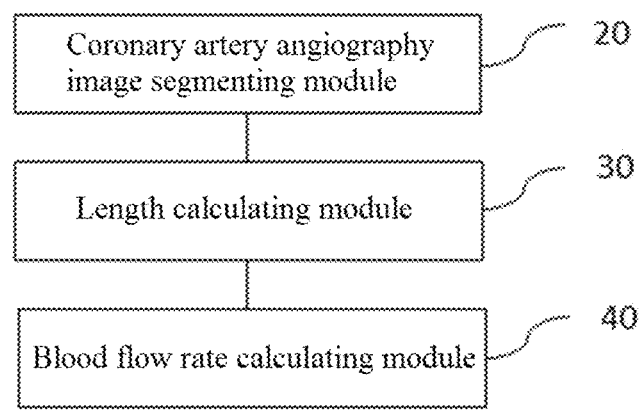
FIG. 14 is a structural schematic diagram of an apparatus for calculating the blood flow rate in a coronary artery according to an embodiment of the present invention.

As shown in FIG. 14, an apparatus for calculating the blood flow rate in a coronary artery according to an embodiment of the present invention for implementing the method for calculating the blood flow rate in a coronary artery according to an embodiment of the present invention comprises a coronary artery angiography image segmenting module 20, a length calculating module 30 and a blood flow rate calculating module 40.

The coronary artery angiography image segmenting module 20 is used for acquiring an angiography image of the coronary artery, segmenting the angiography image of the coronary artery by using deep learning, and obtaining segmented images of a main vessel.

The length calculating module 30 is used for calculating the length of the main vessel in each segmented image frame on the basis of the segmented images of the main vessel.

The blood flow rate calculating module 40 is used for obtaining the blood flow rate of the main vessel on the basis of the calculated change of the lengths of the main vessel with time.

Preferably, the apparatus for calculating the blood flow rate in a coronary artery further comprises a display apparatus, and the display apparatus is used for displaying type selection of the main vessel of the coronary artery for a user;

the coronary artery angiography image segmenting module 20 is used for acquiring the angiography image of the coronary artery, and segmenting the angiography image of the coronary artery by using deep learning on the basis of the type, selected by the user, of the main vessel to obtain the segmented images of the main vessel.

Preferably, the coronary artery angiography image segmenting module 20 is used for judging whether the projection angle of the angiography image of the coronary artery is within a required angle range of the main vessel of this type or not on the basis of the type, selected by the user, of the main vessel; wherein if the projection angle of the angiography image of the coronary artery is within the required angle range of the main vessel of this type, the angiography image of the coronary artery is segmented by using deep learning, and the segmented images of the main vessel are obtained; and if the projection angle of the angiography image of the coronary artery is not within the required angle range of the main vessel of this type, the display apparatus is used for displaying a prompt message for the user.

Preferably, the coronary artery angiography image segmenting module 20 is used for acquiring feature maps with different resolutions of the angiography image of the coronary artery by means of an encoder structure of a U-Net model, and then refining and combining the feature maps with different resolutions by utilizing a RefineNet module to obtain the segmented images of the main vessel.

Preferably, the length calculating module 30 is used for extracting the segmented images of the main vessel to obtain an angiography image of a blood vessel skeleton, calculating the length of the blood vessel skeleton in the angiography image of the blood vessel skeleton to obtain the lengths of the main vessel in pixels, and calculating in combination with a calibration factor of the image to obtain the actual physical length of the main vessel.

Preferably, the blood flow rate calculating module 40 is used for obtaining a change curve of the length of the main vessel with time by taking time as an abscissa and taking the lengths of the main vessel in the segmented images of the main vessel as an ordinate, selecting a preset section of the change curve of the lengths of the main vessel with time, and calculating the slope of the preset section to obtain the blood flow rate of the main vessel.

Preferably, the blood flow rate calculating module 40 is used for obtaining a change curve of the lengths of the main vessel with frame number by taking the frame number of the segmented images of the main vessel as an abscissa and taking the actual lengths of the main vessel as an ordinate, and converting the abscissa in the change curve of the lengths of the main vessel with frame number into time on the basis of frame frequency information to obtain the change curve of the lengths of the main vessel with time.

Preferably, the blood flow rate calculating module 40 is used for smoothing the change curve of the lengths of the main vessel with time to obtain a smooth curve of the change curve of the lengths of the main vessel with time; obtaining the maximum value of the lengths of the main vessel on the smooth curve; selecting the section, with the lengths of the main vessel on the smooth curve being a preset value of the maximum value of the lengths of the main vessel, as a preset section area, wherein the section, opposite to the preset section area on the smooth curve, of the change curve of the lengths of the main vessel with time is a preselected section; judging whether the preselected section contains one cardiac cycle or not according to the electrocardio information of the coronary artery corresponding to the preselected section, wherein if the preselected section does not contain one cardiac cycle, it is determined that the preselected section is the preset section; and performing straight line fitting on the preset section, and calculating the slope of a straight line obtained by fitting to obtain the blood flow rate of the main vessel.

Preferably, if the preselected section contains one cardiac cycle, then the preset section is obtained by extending toward two ends of the preselected section by the length of half of the cardiac cycle respectively by taking the center of the preselected section as a starting point.

Preferably, the apparatus for calculating the blood flow rate in a coronary artery further comprises a display apparatus, the display apparatus is used for displaying the change curve of the lengths of the main vessel with time, the angiography image of the coronary artery and the electrocardio information of the coronary artery corresponding to the angiography image of the coronary artery for the user, and the user checks the angiography image of the coronary artery corresponding to the preset section, and the electrocardio information of the coronary artery, verifies the selected preset section, and manually adjusts the selected preset section if the preset section is unreasonably selected.

The angiography image of the coronary artery is segmented by using deep learning to obtain the segmented images of the main vessel, the length of the main vessel in each image frame are calculated, and further the blood flow rate of the main vessel is obtained on the basis of the change of the lengths of the main vessel with time, by the apparatus for calculating the blood flow rate of the coronary artery, the automation of the calculation of the blood flow rate of the coronary artery is realized, the calculated blood flow rate of the coronary artery is more accurate, and the calculation method is simple.

Figure 15:
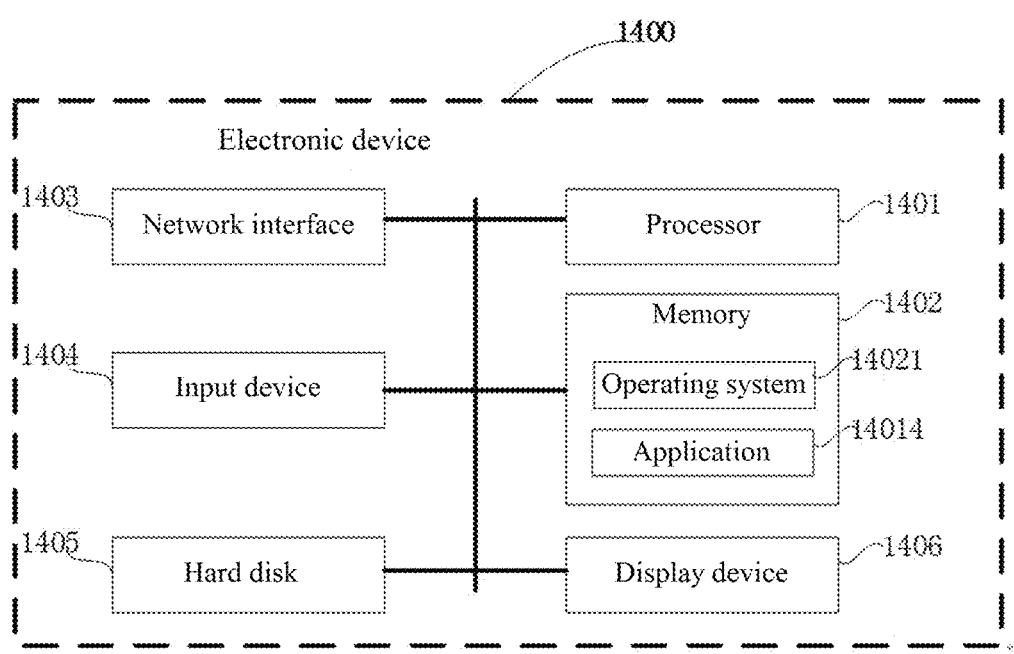
FIG. 15 is a structural schematic diagram of an electronic device according to an embodiment of the present invention.

As shown in FIG. 15, based on the inventive concept the same as that of the method for calculating the blood flow rate in a coronary artery, the present application further provides an electronic device 1400, the electronic device 1400 comprises one or more processors 1401 and one or more memories 1402, and the memories 1402 store computer readable codes, wherein the computer readable codes perform the following processing when executed by the one or more processors 1401:

S1, acquiring an angiography image of the coronary artery, segmenting the angiography image of the coronary artery by using deep learning, and obtaining segmented images of main vessel;

S2, calculating the length of the main vessel in each segmented image frame on the basis of the segmented images of the main vessel; and

S3, obtaining the blood flow rate of the main vessel on the basis of the calculated change of the lengths of the main vessel with time.

Preferably, the S1 specifically comprises: acquiring the angiography image of the coronary artery, displaying type selection of the main vessel of the coronary artery, and segmenting the angiography image of the coronary artery by using deep learning on the basis of the type, selected by the user, of the main vessel to obtain the segmented images of the main vessel.

Preferably, the S1 further comprises: judging whether the projection angle of the angiography image of the coronary artery is within a required angle range of the main vessel of this type or not on the basis of the type, selected by the user, of the main vessel; wherein if the projection angle of the angiography image of the coronary artery is within the required angle range of the main vessel of this type, the angiography image of the coronary artery is segmented by using deep learning to obtain the segmented images of the main vessel; and if the projection angle of the angiography image of the coronary artery is not within the required angle range of the main vessel of this type, a prompt message is displayed.

Preferably, the step of segmenting the angiography image of the coronary artery by using deep learning to obtain the segmented images of the main vessel specifically comprises:

acquiring a plurality of feature maps with different resolutions of the angiography image of the coronary artery by means of an encoder structure of a U-Net model, and further refining and combining the plurality of feature maps with different resolutions by utilizing a RefineNet module to obtain the segmented images of the main vessel.

Preferably, the S2 specifically comprises:

S21, extracting the segmented images of the main vessel to obtain an angiography image of a blood vessel skeleton; and S22, calculating the length of the blood vessel skeleton in the angiography image of the blood vessel skeleton to obtain the lengths of the main vessel in pixels, and calculating in combination with a calibration factor of the image to obtain the actual physical length of the main vessel.

Preferably, the S3 specifically comprises:

S31, obtaining a change curve of the lengths of the main vessel with time by taking time as an abscissa and taking the lengths of the main vessel in the segmented images of the main vessel as an ordinate; and S32, selecting a preset section of the change curve of the lengths of the main vessel with time, and calculating the slope of the preset section to obtain the blood flow rate of the main vessel.

Preferably, the S31 specifically comprises:

S311, obtaining a change curve of the lengths of the main vessel with frame number by taking the frame number of the segmented images of the main vessel as an abscissa and taking the actual lengths of the main vessel as an ordinate; and S312, converting the abscissa in the change curve of the lengths of the main vessel with frame number into time on the basis of frame frequency information to obtain the change curve of the lengths of the main vessel with time.

Preferably, the S32 specifically comprises:

smoothing the change curve of the lengths of the main vessel with time to obtain a smooth curve of the change curve of the lengths of the main vessel with time;

obtaining the maximum value of the lengths of the main vessel on the smooth curve, and selecting the section, with the lengths of the main vessel on the smooth curve being a preset value of the maximum value of the lengths of the main vessel, as a preset section area, wherein the section, opposite to the preset section area on the smooth curve, of the change curve of the lengths of the main vessel with time is a preselected section;

judging whether the preselected section contains one cardiac cycle or not according to the electrocardio information of the coronary artery corresponding to the preselected section, wherein if the preselected section does not contain one cardiac cycle, it is determined that the preselected section is the preset section; and performing straight line fitting on the preset section, and calculating the slope of a straight line obtained by fitting to obtain the blood flow rate of the main vessel.

Preferably, if the preselected section contains one cardiac cycle, then the preset section is obtained by extending toward two ends of the preselected section by the length of half of the cardiac cycle respectively by taking the center of the preselected section as a starting point.

Preferably, the change curve of the lengths of the main vessel with time, the angiography image of the coronary artery and the electrocardio information of the coronary artery corresponding to the angiography image of the coronary artery are displayed, and the user checks the angiography image of the coronary artery corresponding to the preset section and the electrocardio information of the coronary artery, verifies the selected preset section, and manually adjusts the selected preset section if the preset section is unreasonably selected.

Further, the electronic device 1400 further comprises a network interface 1403, an input device 1404, a hard disk 1405, and a display device 1406.

The various interfaces and devices described above can be interconnected by bus architecture. The bus architecture can comprise any number of interconnected buses and bridges. Specifically, the bus architecture can connect various circuits of one or more central processing units (CPUs) represented by the processor 1401, and various circuits of one or more memories 1402 represented by the memory 1402 together. The bus architecture can also connect various other circuits such as peripherals, voltage regulators and power management circuits. It will be appreciated that the bus architecture is used for implementing connection communication between these components. The bus architecture comprises a power bus, a control bus, and a status signal bus in addition to a data bus, all of the above content is well known in the art and therefore will not be described in detail herein.

The network interface 1403 can be connected to a network (such as the Internet and the local area network), and related data can be acquired from the network, and be stored in the hard disk 1405.

The input device 1404 can receive various instructions input by an operator, and transmit the instructions to the processor 1401 for execution. The input device 1404 can comprise a keyboard or a clicking device (such as a mouse, a trackball, a touch panel, or a touch screen and the like).

The display device 1406 can display a result obtained by the processor 1401 executing the instructions.

The memory 1402 is used for storing programs and data which are necessary for running of an operating system 14021, and data such as intermediate results in the calculating process of the processor 1401.

It will be appreciated that the memory 1402 in the embodiments of the present application can be either a volatile memory or a nonvolatile memory, or can comprise both a volatile memory and a nonvolatile memory. The nonvolatile memory can be a read only memory (ROM), a programmable read only memory (PROM), an erasable programmable read only memory (EPROM), an electrically erasable programmable read only memory (EEPROM), or a flash memory. The volatile memory can be a random access memory (RAM), which acts as an external cache memory. The memory 1402 of the apparatus and method the described herein is intended to include, without being limited to, these and any other suitable types of memories.

In some embodiments, the memory 1402 stores the following elements, executable modules or data structures, or a subset or expanded set thereof: the operating system 14021 and an application 14014.

The operating system 14021 comprises various system programs, such as a framework layer, a core library layer and a driver layer, and is used for implementing various basic services and processing hardware-based tasks. The application 14014 comprises various applications, such as a browser, and is used for implementing various application services. Programs that implement methods of embodiments of the present application can be included in the application 14014.

The method disclosed in the above embodiments of the present application can be applied to the processor 1401, or can be implemented by the processor 1401. The processor 1401 can be an integrated circuit chip having signal processing capabilities. In the implementation process, the steps of the above method can be performed by integrated logic circuits in the form of hardware or instructions in the form of software in the processor 1401. The processor 1401 can be a general purpose processor, a digital signal processor (DSP), an application specific integrated circuit (ASIC), a field programmable gate array (FPGA) or other programmable logic device, discrete gate or transistor logic device and discrete hardware component, and can implement or perform the methods, steps, and logic block diagrams disclosed in the embodiments of the present application. A general purpose processor can be a microprocessor or the processor can be any conventional processor or the like. The steps of the method disclosed in conjunction with the embodiments of the present application can be directly implemented by a hardware decoding processor, or implemented by a combination of hardware and software modules in the decoding processor. The software modules can be located in a mature storage medium in the art such as a random access memory, a flash memory, a read-only memory, a programmable read-only memory or an electrically erasable programmable memory and a register. The storage medium is located in the memory 1402, and the processor 1401 reads the information in the memory 1402, and implements the steps of the above method in combination with the hardware thereof.

It will be appreciated that the embodiments described herein can be implemented by hardware, software, firmware, middleware, microcode, or a combination thereof. For implementation by hardware, processing units can be implemented within one or more application specific integrated circuits (ASICs), digital signal processors (DSPs), digital signal processing devices (DSPDs), programmable logic devices (PLDs), field programmable gate arrays (FPGAs), general purpose processors, controllers, micro-controllers, microprocessors, other electronic units used for performing the functions described in the present application, or a combination thereof.

With regard to implementation by software, the techniques described herein can be implemented by means of modules (such as procedures and functions) that perform the functions described herein. The software codes can be stored in a memory and executed by a processor. The memory can be implemented within the processor or external to the processor.

In the embodiments of the present application, by the electronic device 1400, the angiography image of the coronary artery is segmented by using deep learning to obtain the segmented images of the main vessel, the length of the main vessel in each image frame are calculated, then the blood flow rate of the main vessel is obtained on the basis of the change of the lengths of the main vessel with time, by the electronic device for calculating the blood flow rate in a coronary artery, the automation of the calculation of the blood flow rate of the coronary artery is realized, the calculated blood flow rate of the coronary artery is more accurate, and the calculation method is simple.

In addition, an embodiment of the present application further provides a computer storage medium, the computer storage medium stores computer readable codes, and the computer readable codes perform the following processing when executed by one or more processors:

S1, acquiring an angiography image of the coronary artery, segmenting the angiography image of the coronary artery by using deep learning, and obtaining segmented images of main vessel;

S2, calculating the length of the main vessel in each segmented image frame on the basis of the segmented images of the main vessel; and S3, obtaining the blood flow rate of the main vessel on the basis of the calculated change of the lengths of the main vessel with time.

When the computer readable codes are executed by the processor, various processes of the above embodiments of the method for calculating the blood flow rate in a coronary artery are implemented, the same technical effects can be achieved, and in order to avoid repetition, detailed processes will not be described here again. The computer storage medium can be a read-only memory (ROM), a random access memory (RAM), a magnetic disk or an optical disk.

In the several embodiments provided in the present application, it should be understood that the disclosed method and apparatus can be implemented in other manners. For example, the above-described apparatus embodiments are merely illustrative, and for example, the division of the units is only one type of logical functional division, and other divisions can be realized in practice, for example, multiple units or components can be combined or integrated into another system, or some features can be ignored, or not executed. In addition, the shown or discussed mutual coupling or direct coupling or communication connection can be indirect coupling or communication connection through some interfaces, devices or units, and can be in an electrical, mechanical or other form.

In addition, functional units in the embodiments of the present application can be integrated into one processing unit, or each unit can be separately and physically included, or two or more units can be integrated into one unit. The integrated unit can be implemented in the form of hardware, or in the form of hardware plus a software functional unit.

The technical features of the above described embodiments can be arbitrarily combined. In order to simplify the description, all possible combinations of the technical features in the above described embodiments are not described. However, as long as these combinations of the technical features do not have contradictions, these combinations should all be considered to be within the scope described in the description.

The above described embodiments express only several embodiments of the present invention, which are described in a more specific and detailed manner, but cannot therefore be understood as a limitation to the scope of the invention patent. It should be pointed out that for those of ordinary skill in the art, on the premise of not departing from the concept of the present invention, several modifications and improvements can be made to the present invention, ad all belong to the scope of protection of the present invention. Therefore, the scope of protection of the invention patent should be subject to the attached claims.

What is claimed is:

1. A method for calculating the blood flow rate in a coronary artery, characterized by comprising the following steps:

S1, acquiring an angiography image of a coronary artery, segmenting the angiography image of the coronary artery by using deep learning, and obtaining segmented images of a main vessel;

S2, calculating the length of the main vessel in each segmented image frame on the basis of the segmented images of the main vessel; and S3, obtaining the blood flow rate in the main vessel on the basis of the calculated change of the lengths of the main vessel with time;

the segmenting the angiography image of the coronary artery by using deep learning to obtain segmented images of main vessel specifically comprises:

acquiring a plurality of feature maps with different resolutions of the angiography image of the coronary artery by means of an encoder structure of a U-Net model, and further refining and combining the plurality of feature maps with different resolutions by utilizing a RefineNet module to obtain the segmented images of the main vessel;

wherein the refining and combining of feature maps is a decoding process.

2. The method for calculating the blood flow rate in a coronary artery according to claim 1, characterized in that the S1 specifically comprises: acquiring the angiography image of the coronary artery, displaying type selection of the main vessel of the coronary artery, and segmenting the angiography image of the coronary artery by using deep learning on the basis of the type, selected by a user, of the main vessel to obtain the segmented images of the main vessel.

3. The method for calculating the blood flow rate in a coronary artery according to claim 2, characterized in that the S1 further comprises: judging whether the projection angle of the angiography image of the coronary artery is within a required angle range of the main vessel of this type on the basis of the type, selected by the user, of the main vessel; wherein if the projection angle of the angiography image of the coronary artery is within the required angle range of the main vessel of this type, the angiography image of the coronary artery is segmented by using deep learning to obtain the segmented images of the main vessel; and if the projection angle of the angiography image of the coronary artery is not within the required angle range of the main vessel of this type, a prompt message is displayed.

4. The method for calculating the blood flow rate in a coronary artery according to claim 1, characterized in that the S2 specifically comprises:

S21, extracting the segmented images of the main vessel to obtain an angiography image of a blood vessel skeleton; and S22, calculating the length of the blood vessel skeleton in the angiography image of the blood vessel skeleton to obtain the lengths of the main vessel in pixels, and calculating in combination with a calibration factor of the image to obtain the actual physical length of the main vessel.

5. The method for calculating the blood flow rate in a coronary artery according to claim 4, characterized in that the S3 specifically comprises:

S31, obtaining a change curve of the lengths of the main vessel with time by taking time as an abscissa and taking the lengths of the main vessel in the segmented images of the main vessel as an ordinate; and S32, selecting a preset section of the change curve of the lengths of the main vessel with time, and calculating the slope of the preset section to obtain the blood flow rate of the main vessel.

6. The method for calculating the blood flow rate in a coronary artery according to claim 5, characterized in that the S31 specifically comprises:

S311, obtaining a change curve of the lengths of the main vessel with frame number by taking the frame number of the segmented images of the main vessel as an abscissa and taking the actual lengths of the main vessel as an ordinate; and S312, converting the abscissa in the change curve of the lengths of the main vessel with frame number into time on the basis of frame frequency information to obtain the change curve of the lengths of the main vessel with time.

7. The method for calculating the blood flow rate in a coronary artery according to claim 5, characterized in that the S32 specifically comprises:

smoothing the change curve of the lengths of the main vessel with time to obtain a smooth curve of the change curve of the lengths of the main vessel with time;

obtaining the maximum value of the lengths of the main vessel on the smooth curve, and selecting a section, with the lengths of the main vessel on the smooth curve being a preset value of the maximum value of the lengths of the main vessel, as a preset section area, wherein the section, opposite to the preset section area on the smooth curve, of the change curve of the lengths of the main vessel with time is a preselected section;

judging whether the preselected section contains one cardiac cycle or not according to electrocardio information of the coronary artery corresponding to the preselected section, wherein if the preselected section does not contain one cardiac cycle, it is determined that the preselected section is the preset section; and performing straight line fitting on the preset section, and calculating the slope of a straight line obtained by fitting to obtain the blood flow rate of the main vessel.

8. The method for calculating the blood flow rate in a coronary artery according to claim 7, characterized in that if the preselected section contains one cardiac cycle, then the preset section is obtained by extending toward two ends of the preselected section by the length of half of the cardiac cycle respectively by taking the center of the preselected section as a starting point.

9. The method for calculating the blood flow rate in a coronary artery according to claim 8, characterized in that the change curve of the lengths of the main vessel with time, the angiography image of the coronary artery and the electrocardio information of the coronary artery corresponding to the angiography image of the coronary artery are displayed, and a user checks the angiography image of the coronary artery corresponding to the preset section, and the electrocardio information of the coronary artery, verifies the selected preset section, and manually adjusts the selected preset section if the preset section is unreasonably selected.

10. A method for calculating blood flow reserve in a coronary artery, characterized in that the blood flow rate of the main vessel in a resting state and the blood flow rate of the main vessel in a hyperemic state are respectively calculated by the method for calculating the blood flow rate in a coronary artery according to any one of claim 1, and the blood flow reserve of the coronary artery is obtained according to the calculated blood flow rate of the main vessel in the resting state and the calculated blood flow rate of the main vessel in the hyperemic state;

preferably, by the method for calculating the blood flow rate in a coronary artery, the blood flow rate of the main vessel in the resting state and the blood flow rate of the main vessel in the hyperemic state are respectively calculated on the basis of the angiography image of the main vessel in the resting state and the angiography image of the coronary artery in the hyperemic state, wherein a time difference between the acquisition time of the angiography image of the coronary artery of the main vessel in the resting state and the acquisition time of the angiography image of the coronary artery of the main vessel in the hyperemic state is not greater than a first time threshold.

11. An electronic device for calculating the blood flow rate in a coronary artery, characterized by comprising:
   one or more processors; and
   one or more memories, storing computer readable codes, wherein the computer readable codes implement the method for calculating the blood flow rate in claim 1 when executed by the one or more processors.

12. An apparatus for calculating the blood flow rate in a coronary artery, characterized by comprising: a coronary artery angiography image segmenting module, used for acquiring an angiography image of a coronary artery, and segmenting the angiography image of the coronary artery by using deep learning to obtain segmented images of a main vessel; a length calculating module, used for calculating the length of the main vessel in each segmented image frame on the basis of the segmented images of the main vessel; and a blood flow rate calculating module, used for obtaining the blood flow rate of the main vessel on the basis of the calculated change of the lengths of the main vessel with time; the coronary artery angiography image segmenting module is used for acquiring a plurality of feature maps with different resolutions of the angiography image of the coronary artery by means of an encoder structure of a U-net model, and further refining and combining the plurality of feature maps with different resolutions by utilizing a RefineNet module to obtain the segmented images of the main vessel; wherein the refining and combining of feature maps is a decoding process.

13. The apparatus for calculating the blood flow rate in a coronary artery according to claim 12, characterized in that the apparatus for calculating the blood flow rate in a coronary artery further comprises a display apparatus, and the display apparatus is used for displaying type selection of the main vessel of the coronary artery for a user;
   the coronary artery angiography image segmenting module is used for acquiring the angiography image of the coronary artery, and segmenting the angiography image of the coronary artery by using deep learning on the basis of the type, selected by the user, of the main vessel to obtain the segmented images of the main vessel.

14. The apparatus for calculating the blood flow rate in a coronary artery according to claim 13, characterized in that the coronary artery angiography image segmenting module is used for judging whether the projection angle of the angiography image of the coronary artery is within a required angle range of the main vessel of this type on the basis of the type, selected by the user, of the main vessel; wherein
   if the projection angle of the angiography image of the coronary artery is within the required angle range of the main vessel of this type, the angiography image of the coronary artery is segmented by using deep learning to obtain the segmented images of the main vessel; and
   if the projection angle of the angiography image of the coronary artery is not within the required angle range of the main vessel of this type, the display apparatus is used for displaying a prompt message for the user.

15. The apparatus for calculating the blood flow rate in a coronary artery according to claim 12, characterized in that the length calculating module is used for extracting the segmented images of the main vessel to obtain an angiography image of a blood vessel skeleton, calculating the length of the blood vessel skeleton in the angiography image of the blood vessel skeleton to obtain the lengths of the main vessel in pixels, and calculating in combination with a calibration factor of the image to obtain the actual physical length of the main vessel.

16. The apparatus for calculating the blood flow rate in a coronary artery according to claim 15, characterized in that the blood flow rate calculating module is used for obtaining a change curve of the lengths of the main vessel with time by taking time as an abscissa and taking the lengths of the main vessel in the segmented images of the main vessel as an ordinate, selecting a preset section of the change curve of the lengths of the main vessel with time, and calculating the slope of the preset section to obtain the blood flow rate of the main vessel.

17. The apparatus for calculating the blood flow rate in a coronary artery according to claim 16, characterized in that the blood flow rate calculating module is used for obtaining a change curve of the lengths of the main vessel with frame number by taking the frame number of the segmented images of the main vessel as an abscissa and taking the actual lengths of the main vessel as an ordinate, and converting the abscissa in the change curve of the lengths of the main vessel with frame number into time on the basis of frame frequency information to obtain the change curve of the lengths of the main vessel with time.

18. The apparatus for calculating the blood flow rate in a coronary artery according to claim 16, characterized in that the blood flow rate calculating module is used for smoothing the change curve of the lengths of the main vessel with time to obtain a smooth curve of the change curve of the lengths of the main vessel with time; obtaining the maximum value of the lengths of the main vessel on the smooth curve; selecting the section, with the lengths of the main vessel on the smooth curve being a preset value of the maximum value of the lengths of the main vessel, as a preset section area, wherein
   the section, opposite to the preset section area on the smooth curve, of the change curve of the lengths of the main vessel with time is a preselected section; judging whether the preselected section contains one cardiac cycle or not according to electrocardio information of the coronary artery corresponding to the preselected section, wherein if the preselected section does not contain one cardiac cycle, it is determined that the preselected section is the preset section; and
   performing straight line fitting on the preset section, and calculating the slope of a straight line obtained by fitting to obtain the blood flow rate of the main vessel.

* * * * *